United States Patent [19]

Reenstierna

[11] 4,162,679

[45] Jul. 31, 1979

[54] METHOD AND DEVICE FOR THE IMPLANTATION OF ONE OR MORE PACEMAKER ELECTRODES IN A HEART

[76] Inventor: Erik G. B. Reenstierna, Borgeby 11, 230 50 Bjärred, Sweden

[21] Appl. No.: 837,476

[22] Filed: Sep. 28, 1977

[30] Foreign Application Priority Data

Sep. 28, 1976 [SE] Sweden ................. 7610696

[51] Int. Cl.² .......................... A61N 1/04
[52] U.S. Cl. ............................. 128/419 P
[58] Field of Search ............ 128/260, 404, 419 P, 128/2 M, DIG. 9, 1.3–1.5

[56] References Cited

U.S. PATENT DOCUMENTS

| 2,671,451 | 3/1954 | Bolger | 128/1.3 |
| 2,897,411 | 7/1959 | Brown et al. | 128/1.4 |
| 3,674,014 | 7/1972 | Tillander | 128/1.3 |
| 3,847,157 | 11/1974 | Calliovette et al. | 128/2 M |

OTHER PUBLICATIONS

Frei et al., "Medical Research Engineering" 4th Quarter, 1966, pp. 11–18.
Driller "IEEE Transactions on Magnetics" vol. 6, No. 2, Jun. 1970, pp. 353–355.

Primary Examiner—William E. Kamm
Attorney, Agent, or Firm—Karl W. Flocks

[57] ABSTRACT

The disclosure relates to a method and device for the transvenous implantation of at least one pacemaker electrode in a heart, the electrode being connected to a body of permanently magnetized or permanently magnetizable material. A magnet is utilized for moving the electrode by means of its magnetic field of force to a selected region in the heart and for causing it to radicate at the selected region of the heart.

6 Claims, 3 Drawing Figures

METHOD AND DEVICE FOR THE IMPLANTATION OF ONE OR MORE PACEMAKER ELECTRODES IN A HEART

The present invention relates to medicine in general, and in particular to a method and device for transvenously inserting (implanting), into a heart, one or more cardiac electrodes which are, each by means of electric line, in communication with or may be placed in communication with a cardiac stimulator (a so-called pacemaker), for transmitting stimulation pulses to the heart.

In the transvenous implantation of the electrode of a pacemaker intended for contact with the inner cardiac muscle tissue, the endocardium, (a so-called stimulation electrode) for pacemaker treatment of the cardiac rhytm, a selected vein, for example, in the neck or arm, is opened and the electrode is inserted into the right-hand ventricle of the heart through the venal opening and the vein in question. The electrode is connected to an electric line which is connected to or may be connected to the pacemaker (either disposed outside the patient's body or operated into the patient's body). This line, being thin and soft, is rigidified by rigidifying means in order to permit guiding of the electrode to the heart, the guiding being supervised by means of X-ray examination of the part of the body in question. This guiding requires well-controlled manual movements and thereby a high level of concentration on the part of the surgeon, which sometimes can take an unnecessarily long time.

The pacemaker-counter electrode intended for cooperation with the stimulation electrode is also sometimes moved with the assistance of the above-mentioned rigidifying means or some other rigidifying means together with the stimulation electrode to a selected region in the heart, for example, the right-hand atrium, whereas in other cases, the counter electrode is placed outside the heart, for example as a part of the pacemaker package in contact with corporal tissue (earthing).

The stimulation electrode is passed through the selected vein up to the apex of the right ventricle and is there brought into electric contact with the endocardium in order to permit stimulation of the heart muscle (myocardium) which determines the cardiac activity. In order that this contact be maintained, the electrode must lie still at the point of contact for a time of sufficient length that it be possible for fibrin to be deposited on and about the electrode and the electrode thus radicate in the selected position of contact. If the electrode does not lie still in the position of contact, fibrin is deposited between the heart tissue and the stimulation electrode, which entails an increase in resistance, so-called threshold value increase, in the electrical connection between the heart tissue and the electrode. As a result, the function of the pacemaker can be weakened or arrested.

In order to make possible such immobilisation of the stimulation electrode, the patient must first and foremost lie still and, secondly, the electrode must be fixed to the heart tissue, since the cardiac activity, that is to say the contraction and expansion of the myocardium, and the blood flow, tend to dislodge the electrode from its contact with the tissue. The requirement that the patient lie still constitutes a serious inconvenience, since the risks for, for example, thrombosis become hereby much greater in many patients.

The prior art devices for fixing the stimulation electrode to the heart tissue have tissue-penetration members, for example, screws or hooks on or adjacent the electrode. It will be readily appreciated that such devices are associated with risks for tissue damage and time-consuming manipulation when the electrode is to be fixed with their assistance in a selected position in electric contact with the tissue or is to be moved from an incorrectly selected position to another, more correct position in the heart; or from a position from which the electrode has been dislodged (as a result of cardiac activity or patient-movement) to another position. It is often not possible to carry out such manipulation, it being necessary to implant a new stimulation electrode in the heart, the old electrode remaining in place notwithstanding.

The object of the present invention is to realize a method for transvenous implantation of at least one electrode in the heart, in particular a stimulation electrode endocardially, by means of which method one or more of the above-mentioned shortcomings in the prior art methods are obviated or at least substantially reduced.

One aspect of the present invention is to provide at least one electrode which is connected to a body of permanently magnetized or permanently magnetizable material, and a magnet whose field of force is allowed to act upon the above-mentioned body for moving the electrode in a selected vein or in the heart.

A further aspect of the present invention is to provide at least one electrode which is connected to a body of permanently magnetized or permanently magnetizable material, and a magnet whose field of force is allowed to act upon the above-mentioned body for making possible the radication of the electrode to a selected region of the heart tissue.

The nature of the present invention and its aspects will be more readily understood from the following brief description of the accompanying drawings, and discussion relating thereto.

In the accompanying drawings:-

Figure 1:
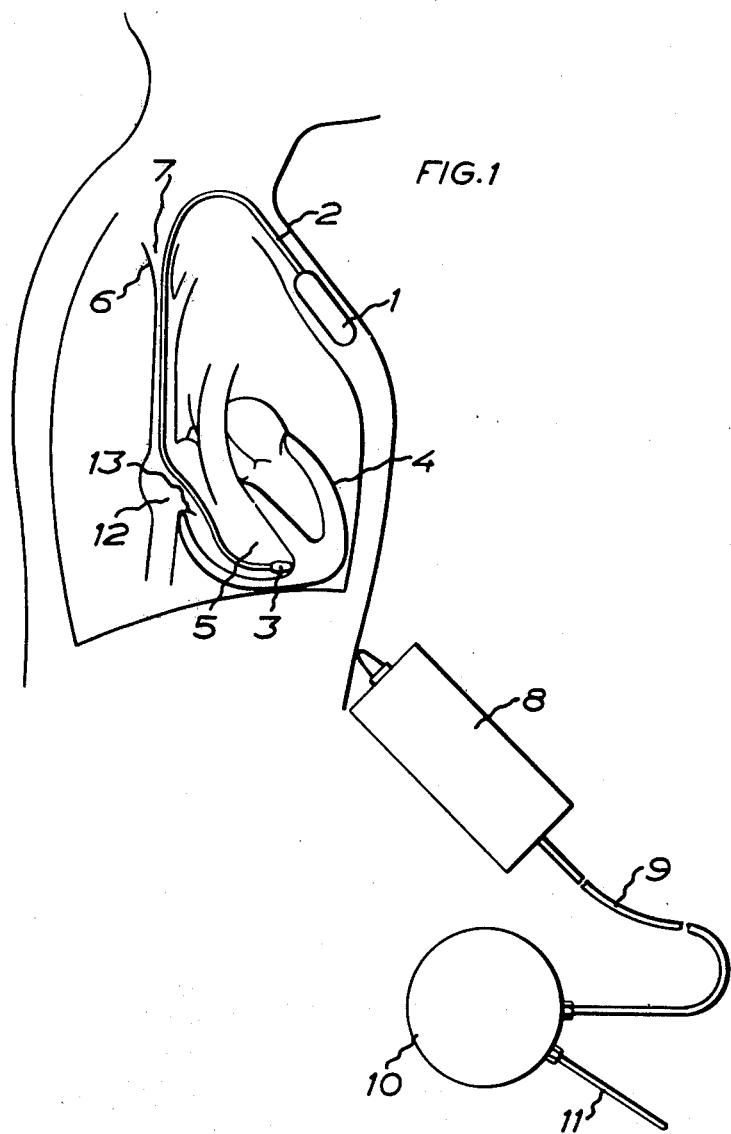
FIG. 1 is a schematic section of a human body with a pacemaker package implanted by operation and with a stimulation electrode brought in position, in accordance with the present invention, at the apex of the right ventricle.
Figure 2:
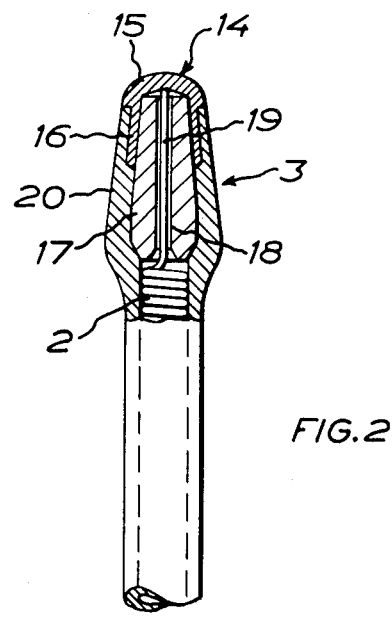
FIG. 2 is a longitudinal section of an electrode head on a larger scale.
Figure 3:
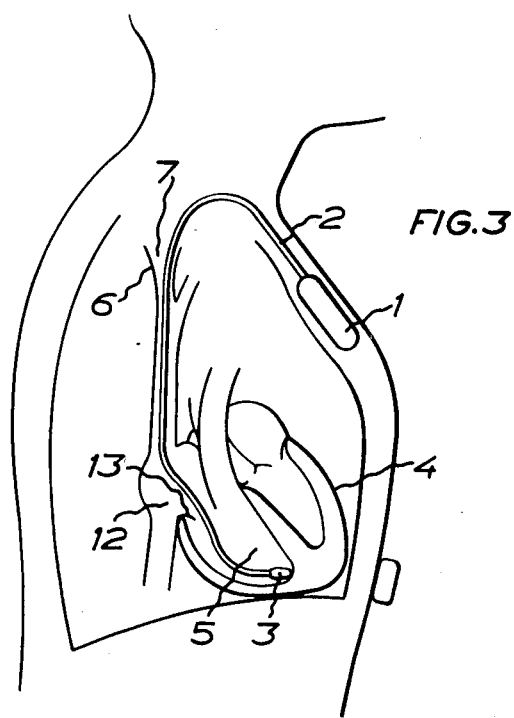

FIG. 3 illustrates a method and device for fixing the electrode in place in the heart. p The reader is now referred to the drawings in which FIG. 1 shows schematically a section through a human trunk with a pacemaker package 1 implanted by operation into the chest and connected by means of an electric line 2 to a stimulation electrode disposed in an electrode-carrying head 3 which contains a permanently magnetizable or permanently magnetized material and which will be described in greater detail below with reference to FIG. 2. The electrode head is inserted in the right-hand ventricle 5 of the heart 4 with electrodes in contact with the endocardium in the apex of the ventricle.

For insertion of the electrode, a selected vein 6 is opened, in the illustrated Example a neck-vein, for example, the external jugular vein, and the electrode head at the distal end of the line 2 from the pacemaker is inserted into the venal opening 7. A magnetic field of force is applied to the electrode head 3 by means of an electromagnet 8 which is connected by means of an electric cable 9 to a foot-actuated regulator 10 provided for regulating the energizing current of the electromagnet and thereby the magnetic field of force produced by the magnet. The regulator is connectible to the A.C. voltage network by means of a cable 11. The electromagnet 8 which is connected in a conventional manner to a rectifier for the alternating current is placed on the exterior of the trunk in the vicinity of the venal opening 7, such that its magnetic field of force, for which the body or the trunk is permeable, influences by attraction the magnetic material in the electrode head.

Under the action of this body or trunk-penetrating magnetic field of force, and by the movement of the electromagnet on the exterior of the trunk from a position in the region of the venal opening in a direction towards the heart, the electrode head is caused to move in the vein in question towards the heart. During the movement of the electrode head towards the heart, the part of the body in question is viewed in a conventional manner by means of X-rays for surveying the movement. The electromagnet may then simply be moved on the exterior of the trunk in the desired direction for correct, substantially centred, guiding of the electrode in the vein. The strength of the magnetic field of force can, for this purpose, also be regulated by the action of the foot regulator 10 which contains (not shown in detail) conventional means for switching the current direction in the electromagnet, and thereby the direction of the magnetic field of force generated by the electromagnet, for making possible reversing of the electrode head and thereby the electrode.

On this point, is thould be noted that, instead of an electromagnet, a permanent magnet can be utilized for the above-mentioned movement of the electrode head and thereby of the electrode in a direction towards or away from the heart, although electromagnets are to be preferred since their magnetic fields are variable and can consequently be adjusted in each position of the electrode on its path to the heart in order to reduce the risk of damage to vessels and tissue to a minimum. The electromagnet may be pointed, as is illustrated, for concentration of the magnet field. By movement of the electromagnet on the exterior of the trunk towards the heart, the electrode head is caused to move along the selected vein, through the vena cava superior, the right-hand atrium 12 and the tricuspid valve 13 to the right ventricle 5 and, more precisely, to the apex of this ventricle, as is illustrated, for contact with the endocardium.

It should be further observed that the electrical line 2, as opposed to prior art lines, need not be associated with any rigidifying means in order to guide the electrode towards the heart, since the electrode can be guided in a highly precise manner to the heart by means of the above-mentioned magnetic field of force without other manipulations than minor movements of the electromagnet 8 on the exterior of the trunk. This also permits of a relatively simple and rapid movement of the electrode past the sensitive and critical constriction formed by the tricuspid valve.

The electrode head 3 is shown in detail in FIG. 2. It comprises a stimulation electrode 14 of an electrically conductive material which is compatible with the liquids of the body and its inner atmosphere, for example a conventional platinum/iridium alloy. As illustrated, the electrode forms the free end of the electrode head and is intended for the previously described contact with the endocardium. The electrode has a bulbous portion 15 with an outwardly rounded end surface in order that the electrode does not catch on parts of the body on its movement from the vein to the apex cordis, and an annular flange 16 which projects rearwardly from the inner edge surface of the bulbous portion so that the electrode body exteriorly has the appearance of a mushroom. The annular flange 16 grasps with tight fit about a substantially cylindrical body 17 of a permanently magnetized or permanently magnetizable material and with a through-hole 18 through which the leading end portion 19 of the electric line 2 (which preferably consists of the same material as the electrode) extends and is electrically-conductively connected, for example, by soldering, to th inner surface of the bulbous portion. Outside the cylindrical body 17, the line is spirally wound and is, at its rear end (not shown), connected to the pacemaker package. A casing 20, of an electrically insulating material which is compatible with the liquids of the body and its inner atmosphere and is permeable to the magnetic field of force, for example, a conventional silicone rubber, surrounds the spirally-wound line, the portion of the body 17 beyond the electrode flange 16 as well as the electrode flange 16 proper, and is connected exteriorly by a smooth transfer surface to the arched end surface of the bulbous portion 15 of the electrode. For constant connection of the casing portion to the body 17 and the flange 16, this casing portion can be vulcanized in place. The body 17 is preferably provided, at least at its portion located inside the flange 16, with a surface layer of some insulator material so that the electric current between the electrode 14 and the line 2 cannot pass via the body 17.

The body 17 can consist of any given permanently magnetizable or permanently magnetized metal or metal alloy; however the rare earth metals are to be preferred such as yttrium, lanthanum or cobalt, or alloys thereof, since these metals and alloys have a powerful residual magnetism after magnetization, which is desirable in view of the fact that the electrode may perhaps be in place in the heart for several years and can require further movement in a manner which will be described below.

The movement of the electromagnet 8 on the trunk is preferably carried out such that the magnetic poles of the body 17 under the action of the field of force of the electromagnet 8 are localized to substantially the ends of the body 17 if the body 17 has not earlier, prior to insertion in the vein, been magnetized.

It should be observed that, instead of the centrally disposed hole in the body 17, some other opening can be provided in and along the body 17 which allows of direct electric connection between the leading end portion of the line and the electrode, for example, a radial channel or groove in the outer surface of the body which can accommodate the end portion of the line. It is even possible to provide the electrode outside the body; however it is essential that the connection between the electrodes and the line be direct, that is to say without interjacent material which would increase the resistance to the electric current between the line and the electrode and form a galvanic element with the electrode, which would lead to oxidation and rapid consumption of the energy which is supplied by the battery of the pacemaker.

A preferred method for forming the body 17 is sintering of the metal in question in pulverulent form, since it may be difficult to produce a metal piece with the above-mentioned hole or channel by machine working.

The sintering tool has, in this instance, a projection or bead with draught for forming the hole or channel.

Once the electrode has been brought into contact with the endocardium in the manner described with reference to FIG. 1, this electrode is fixed at the point of contact with the assistance of a permanent magnet 21 (FIG. 3) of preferably the same material as that of the permanently magnetized body 17. The permanent magnet 21 is fixed on the exterior of the patient's body in a suitable manner, for example, by means of tape or a bandage passed around the patient's body, in the region opposite the apex cordis such that the field of force of the magnet attracts the body 17 and thereby the electrode 14. The magnetic field of force of this permanent magnet is adapted such that it attracts the magnetic body 17 in the electrode head with a force which is sufficient to retain the electrode in the selected point of contact with the endocardium against the action of the forces from the unceasingly moving myocardium and the action of patient movements, such that the electrode, after a certain time, is given the opportunity to radicate itself to the point of contact by fibrin deposition on and about the electrode.

A highly essential advantage with this electrode fixation method and device is that the patient need not be confined to bed during the time the electrode radicates to the endocardium by fibrin deposition, since the forces from the permanent magnet 21 keep the electrode at the contemplated point of contact, despite patient movement and cardiac activity. This differs from the fixation devices mentioned by way of introduction which are not associated with forces independent of patient movement and cardiac activity for retaining the electrode and which thereby require that the patient be confined to bed during the fibrin deposition time, which entails int. al. a risk for thrombosis.

If during the years of use, the threshold value of the electrode is raised, that is to say if fibrin grows in between the electrode and the endocardium and results in an increase in resistance, it is possible with the device according to the present invention, to move the electrode. For this purpose, the polarity of the electromagnet 8 is reversed such that the field of force generated by the electromagnet can repell the electrode head and thereby the electrode from the radicated position, whereafter the polarity of the electromagnet 8 is once again switched for attraction of the body 17 and thereby for movement of the electrode 14 to a different position in electric contact with the endocardium. Thus, in the event of the above-mentioned increase in resistance, the electrode need not, as opposed to the hitherto utilized methods, be left in the heart and a new electrode implanted in the heart, it being possible in a simple fashion to move one and the same electrode to a new site.

In the above discussion, it has been presupposed that the counter electrode intended for cooperation with the stimulation electrode is disposed, in a manner which is not shown but which is known to the skilled reader, on the pacemaker package 1 proper. However, it is the intention that the spirit and scope of the present invention also embrace such an arrangement in which the counter electrode, with its own insulated line, is mechanically connected to the stimulation electrode for movement, together with the latter, to a selected region in the heart with the assistance of the magnetic field of force which is applied to the magnetic body of the stimulation electrode; as well as an arrangement in which the counter electrode is also associated with a magnetic body for separate movement of the counter electrode to a selected site in the heart.

What I claim and desire to secure by letters patent is:

1. A method of transvenously implanting at least one pacemaker electrode in a heart with said electrode electrically connectible, by means of an electric line, to said pacemaker for transferring stimulation pulses to the heart, comprising the steps of inserting the electrode which is connected to a body of material actuable by a magnetic field of force in a selected vein, applying a magnetic field of force and guiding said electrode and connected body of material to a selected region of the heart, applying and holding a permanent magnet to the body of the patient to maintain said electode and connected body of material in contact with the selected region of the heart for the period of time required for growth of body tissue which will maintain electrode positioning.

2. The method of claim 1 further including the step of removing the permanent magnet from the outside of the body of the patient after implantation of the electrode body tissue.

3. The method of claim 2 further including the steps of applying a magnetic field of force of reverse polarity and guiding said electrode and connected body of material away from said first mentioned selected region of the heart and implanting body tissue to a different selected region of the heart.

4. The method as recited in claim 1, wherein said body of material is a permanently magnetized material.

5. The method as recited in claim 1, wherein said body of material is a permanently magnetizable material.

6. The method as recited in claim 1, wherein the magnetic field of force is variable and derives from an electromagnet.

* * * * *